United States Patent [19]

Mandroian

[11] 4,392,791

[45] Jul. 12, 1983

[54] PRESSURE PUMPING AND PRIMING PUMP APPARATUS

[76] Inventor: Harold Mandroian, 2137 Los Amigos, La Canada, Calif. 91001

[21] Appl. No.: 300,412

[22] Filed: Sep. 8, 1981

[51] Int. Cl.³ .................................................. F04B 43/10
[52] U.S. Cl. ....................................... 417/379; 417/458; 417/540
[58] Field of Search .............. 417/379, 458, 479, 540, 417/542, 543

[56] References Cited

U.S. PATENT DOCUMENTS

| | | |
|---|---|---|
| 3,250,224 | 5/1966 | Phillips et al. .................. 417/542 X |
| 3,898,017 | 8/1975 | Mandroian .......................... 417/65 |
| 4,265,601 | 5/1981 | Mandroian .......................... 417/379 |

Primary Examiner—Leonard E. Smith
Attorney, Agent, or Firm—Nilsson, Robbins, Dalgarn, Berliner, Carson & Wurst

[57] ABSTRACT

A pump apparatus for transferring precise amounts of fluid from a container to a patient has a defined volume pump chamber divided by a first diaphragm to define a first chamber and a second chamber. A pumped fluid enters the first chamber through a one-way valve as the first chamber volume increases and is exhausted through a second one-way valve as the first chamber volume decreases. A third one-way valve is coupled to the first and second one-way valves in such a way as to prevent the pumped fluid from flowing through the pump in response to a pressure head at the input or output ports. A priming chamber is divided by a second diaphragm to define first and second sections, respectively. A passageway extends between the first section and the passageway connecting the second and third one-way valves. The second section is coupled to either a pressure varying source to prime the pump by causing the diaphragm to move or to a passive pressure sink to effect damping and smoothing of the pumped fluid pressure at the output port. Control circuitry may be provided to vary the pulse repetition rate, the pulse width, or the pulse amplitude to control the pumping rate. A pressure transducer may be coupled to the second section to provide a feedback control signal to the control circuitry.

10 Claims, 7 Drawing Figures

PRESSURE PUMPING AND PRIMING PUMP APPARATUS

BACKGROUND OF THE INVENTION

The present invention relates to pumps and pumping systems and, in particular, to a pump apparatus which self-primes in its active mode and causes variations in the pressure of the pumped fluid to be damped in its passive mode.

Fluid pumps are typically based upon the use of a rotating or reciprocating device such as an impeller which is bearing mounted and driven by some motive means such as an electric motor. Such mechanical pumps, while reasonably efficient, experience wear of the moving parts and are accompanied by significant levels of audible noise.

In order to solve the problems of wear, a pump having essentially no moving parts was developed and is disclosed in my U.S. Pat. No. 3,898,017, issued Aug. 5, 1975. In that patent, a heater ribbon is placed in a chamber containing the pumped fluid. With pumping occurring by intermittently heating the heater ribbon. While this pump arrangement is acceptable in many applications, direct contact between the heater ribbon and the pumped fluid may not be desirable in some medical applications. Such is the case when the pumped fluid has delicate or fragile structure or which is subject to breakdown in the presence of high temperature. In addition, isolation of the heater ribbon and pumped fluid may be necessary to maintain a sterile environment for the pumped fluid.

A pump which solved these and other problems is disclosed in U.S. Pat. No. 4,265,601 which patent is hereby incorporated by reference.

While this improved pump provides accurate pumping for medical applications it was desired to improve the pump to provide a more constant pressure of the pumped fluid at the exit port to reduce the acceleration and deceleration of the pumped fluid thereby decreasing the load requirements on the pump caused by such peaking. Additionally, it was desired to provide an improved bleeding or priming capability so that bubbles could be quickly purged from the valves and various pump and system passageways prior to use.

In order to provide such improved operation, a damping-priming chamber was incorporated which had a substantially larger pumping volume than the pumping chamber but having a similar construction and mode of operation whereby the pressure of a second pumping fluid could be increased to deflect a diaphragm in the priming-damping chamber. The volume of fluid moved on each diaphragm deflection is preferrably greater than the combined volumes of the valves and connecting passageways in the pump apparatus. Thus, utilizing such a priming-damping chamber the pump can be purged of bubbles and can be primed for operation after just one or two cycles or deflections of the diaphragm in the priming-damping chamber. In addition, the remainder of the pumping system including the connecting tubes between the reservoir and the patient can be be quickly purged of air within just a few pumping cycles.

Additionally, the priming-damping chamber provides a pumped fluid sink whereby rapid increases in pressure of the pumped fluid are abated and moderated by the deflection of the diaphragm in the priming-damping chamber. Subsequently, when the pressure of the pumped fluid decreases the diaphragm in the damping-priming chamber begins to return to the non-deflected state, thereby maintaining the pressure of the pumped fluid for an additional period of time. Thus, the pressure of the expelled pump fluid is damped in that it is maintained at a more constant level over a longer period of time without drastic pressure changes in the pumped fluid being expelled. Such drastic changes (i.e., acceleration and deceleration of the pumped fluid) require the pumps to exert a substantially greater force. Therefore, by incorporating the priming-damping chamber, the load requirements on the pump are significantly reduced.

SUMMARY OF THE INVENTION

The present invention comprises a pumping apparatus for moving a pumped fluid from a reservoir to a destination in response to variations in the pressure of a first pumping fluid and for being primed in response to variations in the pressure of a second pumping fluid. The pumping apparatus in accordance with the invention includes a pump member having an input port for receiving pumped fluid from the reservoir, an exit port for expelling pumped fluid to the destination, a pumping chamber, a priming-damping chamber, an input passageway, an exit passageway and a passageway network between the input passageway and the exit passageway. A first diaphragm is provided to bifurcate the pumping chamber to thereby define a first pumping chamber section for receiving the pumped fluid and a second pumping chamber section for receiving the first pumping fluid. A variable pressure means is then provided for intermittently varying the pressure of the first pumping fluid for intermittently increasing the volume of the second pumping chamber section. This increases the pressure of the pumped fluid causing it to be expelled from the first pumping chamber section. Thereafter, the volume of the second pumping chamber section is decreased to decrease the pressure of the pumped fluid and draw it into the first pumping chamber section. A first valve is positioned between the input passageway and the passageway network and is responsive to the pressure of the pump fluid in the first pumping chamber section. A second valve is also positioned in the passageway network for being responsive to the pressure of the pumped fluid in the first pumping chamber section. The first valve is arranged for being opened when the second valve closes and the first valve is arranged for being closed when the second valve opens. A third valve is coupled between the exit passageway and the second valve in the passageway network for preventing pumped fluid flow through the pump member in response to a pressure head at the input or exit ports. The third valve is coupled to close at least one of the first, second or third valves in response to the pressure head at the input or exit ports. Finally, a second diaphragm is provided for bifurcating the priming-damping chamber to thereby define a first priming chamber section for receiving pumped fluid and a second priming chamber section for receiving the second pumping fluid. The first priming chamber section is interconnected to the passageway network between the second and third valves whereby the pressure of the pumped fluid in the exit passageway is altered in response to deflections of the second diaphragm.

BRIEF DESCRIPTION OF THE DRAWINGS

The invention will be better understood from the detailed description below taken in conjunction with the drawings where like reference characters refer to like parts throughout and in which.

DETAILED DESCRIPTION OF THE PREFERRED EMBODIMENTS

Figure 1:
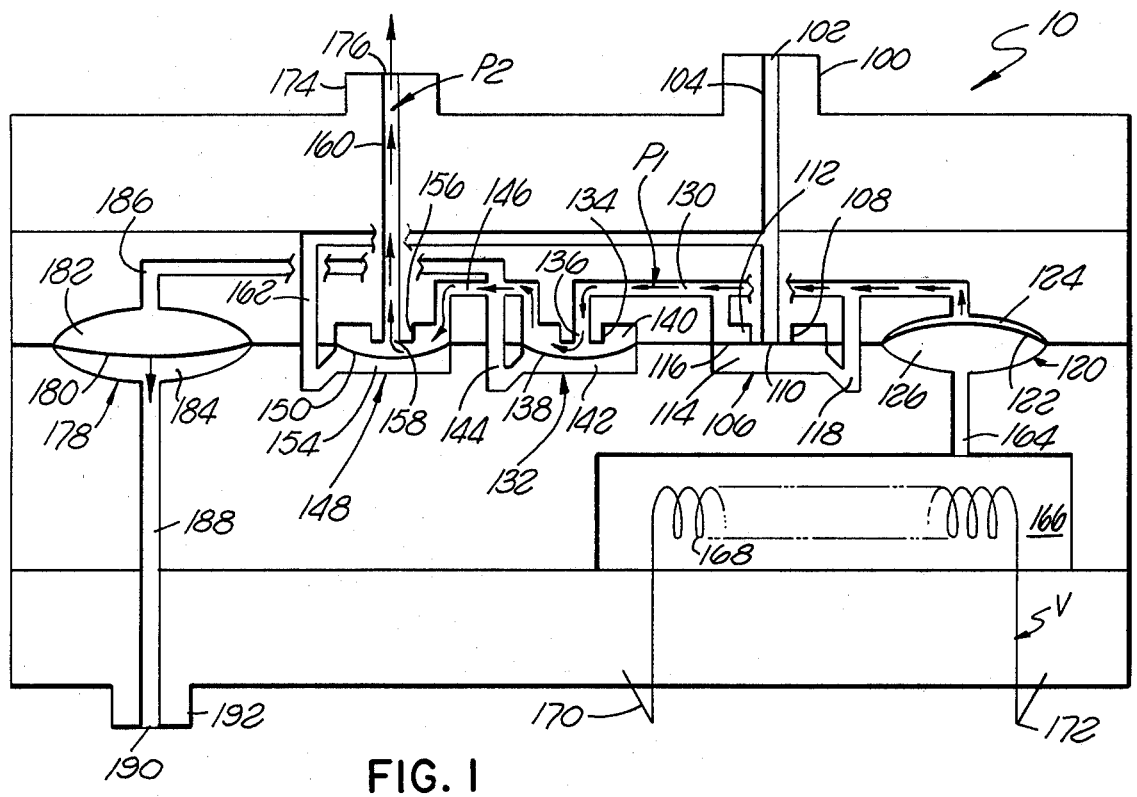
FIG. 1 is a cross sectional side view of a pump apparatus incorporating a priming-damping chamber shown expelling a pumped fluid from an exit port.
Figure 2:
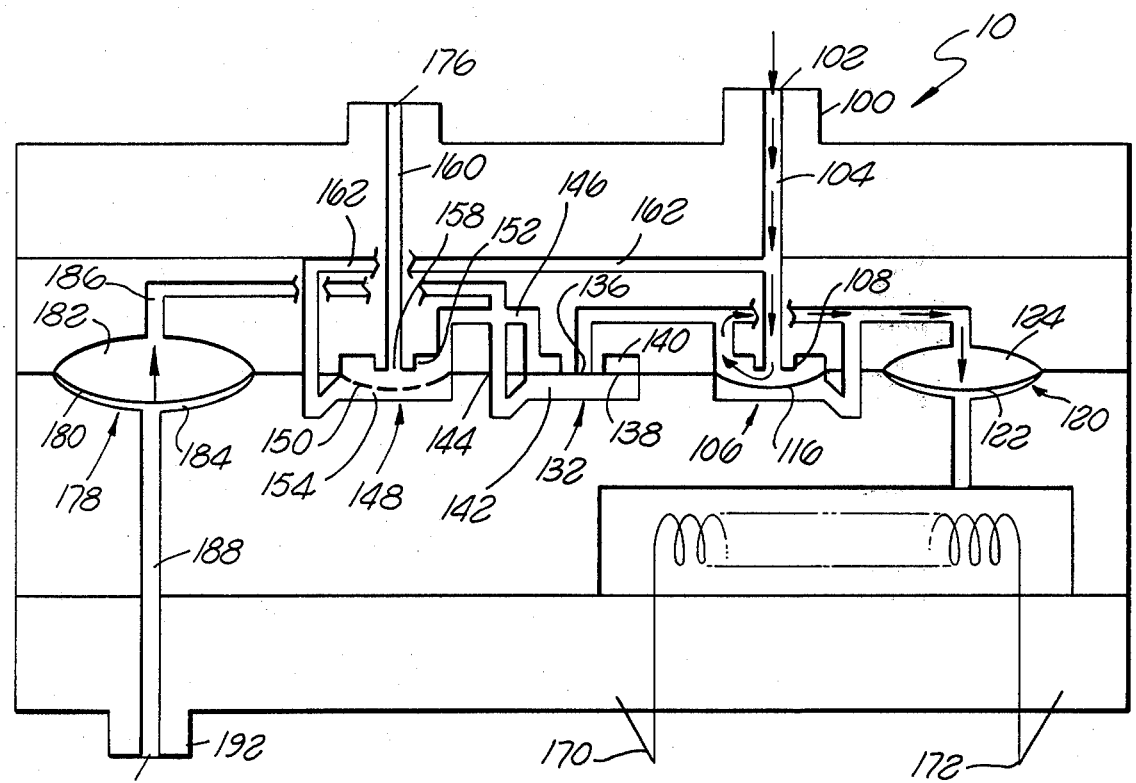
FIG. 2 is a cross sectional side view of the pump apparatus in accordance with the invention shown intaking pumped fluid through the input port.

Referring first to FIGS. 1 and 2, a cross section of one embodiment of the pump apparatus 10 in accordance with the invention has a pump chamber 120, an input valve 106, an output valve 132, a flow-through prevention valve 148 and a priming-damping chamber 178. Each of the valves has a valve chamber preferbly having a precisely defined volume. A valve boss with a passageway port in its end extends into the valve chamber. A valve diaphragm is positioned in the valve chamber across the passageway port of the valve boss to bifurcate the valve chamber into a fluid flow section and a fluid pressure section. Each valve is in a normally closed position with the diaphragm positioned over the passageway port of the valve boss.

More specifically, the input valve 106 has an input valve boss 108 with an input passageway port 110 in its end. The input passageway port 110 is the terminus of an input passageway 104. Pumped fluid enters the input passageway 104 through an input port 102 in the end of an input boss 100.

An input valve diaphragm 116 bifurcates the input valve chamber to define a fluid flow section 112 and a fluid pressure section 114. A pressure equalizing passageway 118 is interconnected between the fluid flow section 112 and the fluid pressure section 114 so that the input valve diaphragm 116 will be displaced from its normally closed position over the input passageway port 110 only when there is a pressure differential between the pumped fluid in the input passageway 104 and the pumped fluid pressure in the valve chamber.

The pump chamber 120 is bifurcated by a pump diaphragm 122 into a first pumping chamber section 124 and a second pumping chamber section 126. A flow passageway 130 is then interconnected to provide unobstructed pumped fluid communication between the first pumping chamber section 124, the fluid flow section 112 and the fluid pressure section 114 of the input valve 106.

The flow passageway 130 terminates at a passageway port 136 in the end of a second valve boss 134 which extends into the valve chamber of the output valve 132. An output valve diaphragm 138 bifurcates the output valve 132 into a fluid flow section 140 and a fluid pressure section 142. The valve diaphragm 138 extends across the passageway port 136 for maintaining the output valve 132 in a normally closed state.

A pressure equalizing passageway 144 provides pumped fluid communication between the fluid flow volume 140 and the fluid pressure section 142 so that the valve diaphragm 138 moves away from the passageway port 136 only when a sufficient differential exits between the pumped fluid pressure in the flow passageway 130 and the pumped fluid pressure in the valve chamber of the output valve 132.

The flow-through prevention valve 148 similarly has a valve chamber bifurcated by a diaphragm 150 which is positioned across a passageway port 158 in the end of a flow-through prevention valve boss 156. The diaphragm 150 bifurcates the valve chamber for defining a fluid flow section 152 and a fluid pressure section 154. A flow passageway 146 interconnects the fluid flow section 140 of the output valve 132 with the fluid flow section 152 of the flow-through prevention valve 148. A pressure equalizing passageway 162 interconnects the fluid pressure section 154 to the input passageway 104.

The passageway port in the flow-through prevention valve boss 156 is the start of an exit passageway 160 which extends through the pump apparatus and has a terminus at an exit port 176 in the end of an exit passageway boss 174.

The priming pump 178 in accordance with the invention has a priming pump chamber bifurcated by a diaphragm 180 into a first priming chamber section 182 and a second priming chamber section 184. A pumped fluid passageway 186 interconnects the first priming chamber section 182 to the flow passageway 146 to allow pressure to be exerted on the pumped fluid in the flow passageway 146 or to allow pressure relief and hence damping and smoothing of pressure variations in the pumped fluid flowing in the flow passageway 146 when the diaphragm 180 is moved in response to an outside force or is moved in response to the pressure of the pumped fluid in the flow passageway 146, respectively. The second priming chamber section 184 is then by a passageway 188 to an external priming port 190 which terminates in the end of a boss 192.

In order to move the pumped fluid through the pump apparatus 10, a pumping fluid is provided in a heating chamber 166 interconnected to the second pumping chamber section 126 by a passageway 164. A heating filament or ribbon 168 positioned in the heating chamber 166 is electrically coupled between a pair of terminals 170 and 172 to which an electric power source (not shown) is attached to provide intermittent electrical pulses to the heating element 168.

Referring to FIG. 1, when an electrical pulse is applied to the heating element 168, the pumping fluid in the heating chamber 166 heats causing the pump diaphragm 122 to be displaced in such a way that the volume of the first pumping chamber section 124 decreases causing the pumped fluid to be forced out of the first pumping chamber section 124 into the flow passageway 130. As a resullt, the output valve diaphragm 138 opens allowing the pumped fluid to pass through the flow passageway 146 to exert pressure against the flow-through prevention valve diaphragm 150. The diaphragm is thereupon displaced downwardly allowing the pumped fluid to flow out the exit passageway 160.

Referring now to FIG. 2, the operation of the pump apparatus 10 when the heating filament 168 is not heating the first pumping fluid is illustrated. In this state, the pumping fluid volume decreases causing the pumping diaphragm 122 to move downward towards the heating chamber 166. This movement causes the volume of the first pumping chamber section 124 to increase which causes pumped fluid to be drawn into the first pumping chamber section 124. As the pumped fluid is drawn into the first pumping chamber section 124, a suction effect causes the output valve diaphragm 138 of the output valve 132 to be held tightly against the passageway port 136, thus assuring that the output valve 132 will remain closed. At the same time, the suction or negative pressure of the pumped fluid causes a pressure differential between the input passageway 104 and the input valve chamber thus causing the diaphragm 116 of the input valve 106 to be displaced downward allowing pumped fluid to flow through the input valve 106 into the first pumping chamber section 124. If there is no pressure head at either the input port 102 or the exit port 176, then the flow-through prevention valve 148 will remain closed.

It will be appreciated that there may be a positive or negative head pressure at either the input or the exit ports 102 or 176, respectively. For example, a sufficiently large positive head pressure at the exit port 176 can result in the opening of the flow-through prevention valve 148. However, the pressure equalizing passageway 144 of the output valve 132 equalizes the pressure in the fluid pressure section 142 in the output valve 132 thus preventing displacement of the valve diaphragm 138 to maintain the output valve in a closed state even though the flow-through prevention valve opens in response to a positive head pressure in the exit passageway 160.

On the other hand, if a positive head pressure exists at the input port 102 the input valve 116 will open as will the output valve 132 in the manner previously described. However, the input passageway 104 is interconnected by the passageway 162 to the fluid pressure section 154 of the flow-through prevention valve 148. Hence, a positive head pressure in the input passageway 104 will be applied in the fluid pressure section 154 but will not be applied in the fluid flow section 152. Therefore, the flow-through prevention valve diaphragm 150 will be forced tightly against the passageway port 158 to keep the flow-through prevention valve closed.

In the above described operating modes of FIGS. 1 and 2, the priming pump diaphragm 180 moves solely in response to variations in the pressure of the pumped fluid in flow passageway 146. There is no externally induced increase or decrease in the second pumping fluid in the second priming chamber 184 to cause independent movement of the diaphragm 180.

Damping and smoothing of the variations in the pumped fluid pressure expelled from port 176 occurs in the following manner: As the pressure of the pumped fluid in the flow passageway 146 increases as occurs in FIG. 1, the pressure of the pumped fluid in the first priming chamber section 182 increases causing the diaphragm 180 to resiliently deflect to increase the volume of the first priming section 182. The increased volume and hence holding capability of the chamber 182 results in a decrease in the pressure of the pumped fluid at the exit port 176. However, as the pressure of the pumped fluid in the flow passageway 146 decreases as occurs in FIG. 2, the diaphragm 180 will begin to return to its undeflected shape thus exerting pressure on the pumped fluid in the flow passageway 146. This, in effect, maintains the pressure of the pumped fluid in the flow passageway 146 above the pressure of the pumped fluid in the flow passageway 130. Thus, the passive movement of the diaphragm 180 causes variations in the pressure of the pumped fluid in the flow passageway 146 to lag and to decrease the magnitude of the variations in the pressure of the pumped fluid at the exit port 176 relative to the pressure of the pumped fluid in the flow passageway 130.

Figure 3A:
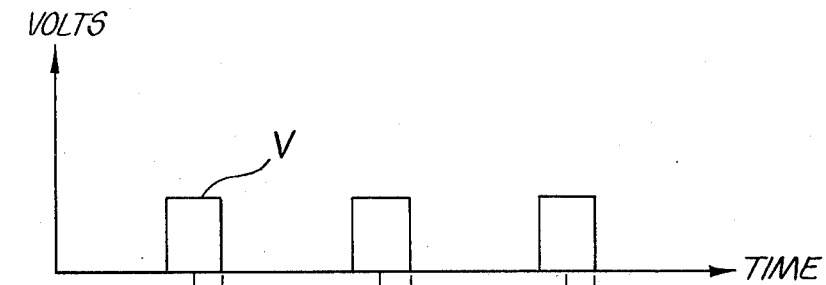
FIG. 3A is a plot of the intermittent voltage signal from a control unit applied to the heating element.
Figure 3B:
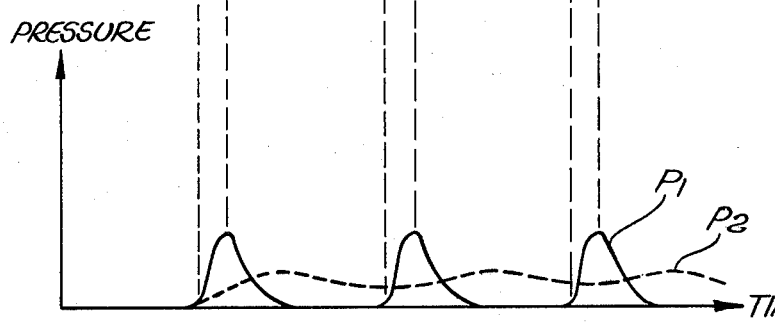
FIG. 3B shows plots of the pressure of the pumped fluid at two locations in the pump resuling from movement of the pumping chamber diaphragm.

This effect is illustrated in FIGS. 3A and 3B where FIG. 3A shows a typical voltage curve of the voltage used to cause the filament or ribbon 168 in FIGS. 1 and 2 to heat. The voltage V which causes the ribbon 168 to heat is preferably a digital signal having a pulse repetition rate, a pulse width and a pulse amplitude which are independently variable to enable control of the amount of heating which occurs in the chamber 166. Of course, it will be appreciated that control over the amount of heating will also result in control over the pumping volume and rate.

As illustrated in FIG. 3B, the pressure P1 of the pumped fluid in the flow passageway 130 will increase in response to pulses in the voltage signal V shown in FIG. 3A. Without the priming chamber 178 the pressure of the pumped fluid at the output port 176 would vary in accordance with the pressure curve P1. However, with the inclusion of the priming chamber 178 in accordance with the invention, the peak values of pressure shown by the curve P1 will be decreased as the diaphragm 180 is deflected downward in response to pressure in the flow passageway 146. Subsequently, the resiliency of the diaphragm and possibly a slight but constant biasing pressure of the second pumping fluid in the chamber section 184, will cause the pressure of the pumped fluid at the output port 176 to be maintained for a period of time as shown by curve P2 in FIG. 3B. Thus, the output pressure of the pumped fluid will be damped and smoothed to yield a more constant pumped fluid pressure.

Figure 4:
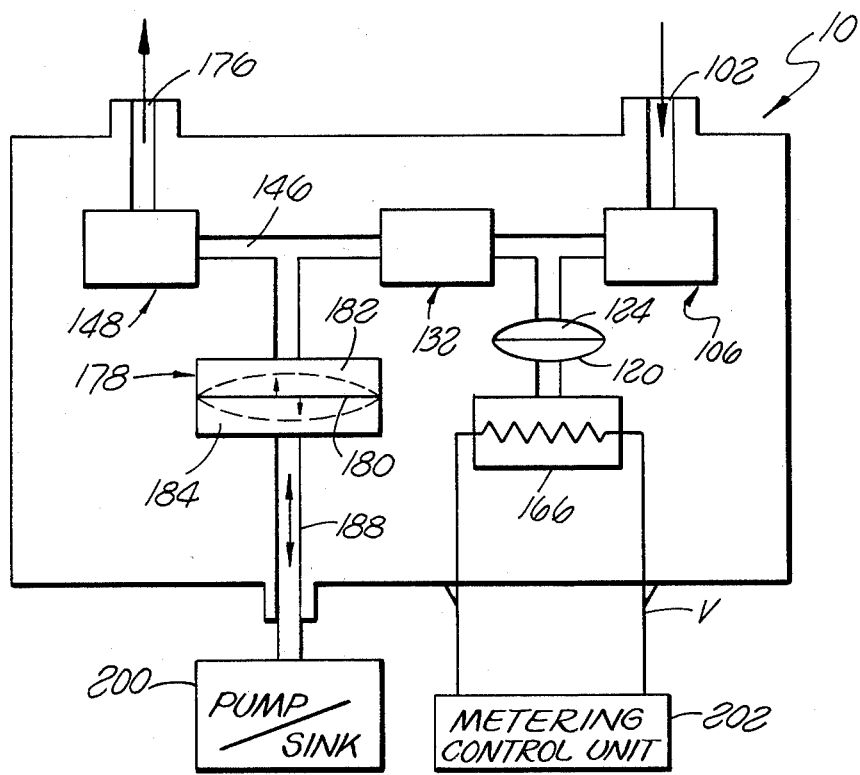
FIG. 4 is a simplified cross sectional side view of the pumping apparatus of FIGS. 1 and 2 wherein the pumping-damping chamber is coupled to an air pump sink.
Figure 5:
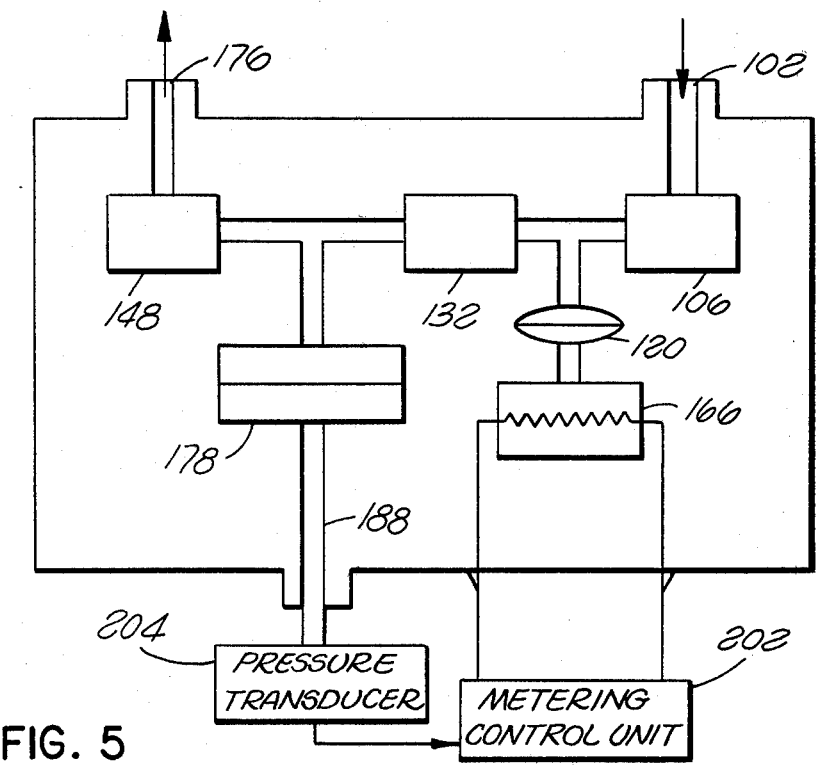
FIG. 5 is a simplified cross sectional side view of the pumping apparatus of FIGS. 1 and 2 incorporating a pressure transducer.

Referring now to FIG. 4, the priming chamber may be used not only to damp and smooth variations in the pressure of the outputted pumped fluid as heretofor described, but may also be used to prime the pump apparatus 10 and eliminate air bubbles from the entire pumping system. Specifically, when the pumping fluid is air the passageway 188 may be interconnected to a suitable pulsating air pump 200 which may, for example, be an aquarium pump. The air pump 200 provides periodic increases and decreases in the pressure of the second pumping fluid in the passageway 188 and hence in the second priming chamber section 184.

More specifically, as the pressure in the passageway 188 and in the second chamber section 184 increase in response to an increase pressure from an air pump or like device 200, the diaphragm 180 deflects upwardly forcing pumped fluid in the passageway 146 through valve 148 and out of the exit port 176. When the pressure in the passageway 188 and second chamber section 184 decreases the diaphragm returns to its undeflected state or possibly deflects in the opposite direction from its previous deflection causing pumped fluid to be pulled in through the input port 102 through the valves 106 and 132 and into the first priming chamber section 182.

By repeating the above process several times, all air bubbles are purged from the system except possibly a small quantity of air which will remain in the pumping chamber section 124. However, that small amount of air will be immediately expelled upon the first several cycles of pumping using the pumping chamber 120.

In the preferred embodiment, the priming chamber will be substantially larger than the pumping chamber and indeed will be preferrably larger than the combined volumes of the various valve chambers and passageways in the pump apparatus 10. Thus, the air can be purged not only from the pump apparatus 10 but from the entire system with no more than several deflections of the diaphragm 180. In such an arrangement, the air pump may be a manually operated plunger or other such device to cuase the diaphragm 180 to deflect several times under manual operation.

Once primed, the air pump is passive acting as a constant pressure sink which is at atmospheric pressure or in the preferred embodiment at a pressure slightly higher than atmospheric pressure to facilitate damping and smoothing of pressure variations in the pumped fluid at the output port 178.

The electrical terminals 170 and 172 may be coupled to a metering or control unit 202 which comprises a pulse generator with suitable potentiometers or the like for varying the pulse width, the pulse amplitude, or the pulse repetition rate of the voltage signal V. Such electronic pulse generators are conventional and will not be herein described in detail.

In accordance with another aspect of the invention, a conventional pressure transducer may be coupled to the passageway 188 to sense the second pumping fluid pressure in the passageway 188. The variations in the pressure of the pumping fluid in the passageway 188 are directly proportional to variations in the pumped fluid pressure at the output or exit port 176. Therefore, the output signal from the pressure transducer is also proportional to the pumped fluid pressure and can be utilized as a feedback signal in a conventional manner to control one or more of the pulse width, pulse repetition rate, or pulse amplitude generated by the metering or control unit 202.

Figure 6:
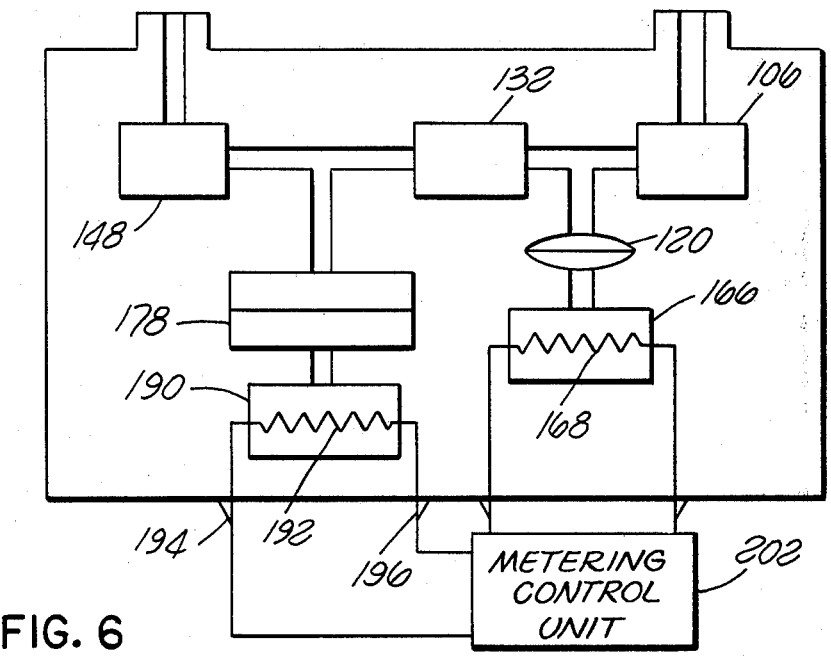
FIG. 6 is a simplified cross sectional side view of the pumping apparatus of FIGS. 1 and 2 modified to incorporate a second heater mechanism to intermittently heat the second pumping fluid.

Finally, referring to FIG. 6 in yet another embodiment of the invention, the priming chamber 178 may be interconnected to a second pumping fluid chamber 190 with a suitable heating ribbon or filament 192 connected to electrical terminals 194 and 196. The electrical terminals 194 and 196 are then coupled to the metering and control unit 202 so that priming utilizing the priming chamber 178 can be accomplished by intermittently heating the ribbon 192 to heat the second pumping fluid in the chamber 190 in the manner previously described in conjunction with chamber 166. In such an embodiment, the pumped fluid can also be pumped utilizing the metering and control unit 202 by simply switching the voltage signal between the filament 168 and the filament 192, either by a manual toggle switch or other suitable means.

The pumped fluid can thus be pumped utilizing one or the other of the pumping chamber 120 or the priming chamber 178. By providing the volume of the pumping chamber 120, so that it is different than the priming chamber volume 178, two entirely different ranges of pumping quantities can be provided in a single pumping unit. Thus, the pumping chamber 120 could provide for pumping within a first range of pumping volumes whereas the priming chamber 178, having a larger but accurately defined pumping chamber, could provide pumping over a second larger range of pumping volumes.

It will also be appreciated that in the normal utilization of the priming chamber 178 the volume of the priming chamber 178 is not accurately defined. However, if the priming chamber 178 is to be used as a means of pumping the pump fluid through the pump then the volume of the priming chamber 178 must be accurate so that volume of fluid pumped on each cycle can be accurately established.

The present invention thus provides an apparatus for pumping precise quantities of fluid from a reservoir to a destination and is particularly applicable in intravenous applications where the rate and quantity of fluids introduced into a patient are critical.

What is claimed is:

1. A pumping apparatus for moving a pumped fluid from a reservoir to a destination in response to variations in the pressure of a first pumping fluid and for being selectively primed in response to externally impressed variations in the pressure of a second pumping fluid comprising:

a pump member having
  an input port for receiving pumped fluid from the reservoir,
  an exit port for expelling pumped fluid to the destination,
  a pumping chamber,
  a priming-damping chamber,
  an input passageway,
  an exit passageway, and
  a passageway network between the input passageway and the exit passageway;
a first diaphragm bifurcating the pumping chamber for defining a first pumping chamber section for receiving the pumped fluid and a second pumping chamber section for receiving the first pumping fluid,
variable pressure means for intermittently varying the pressure of the first pumping fluid for alternately increasing the volume of the second pumping chamber section to increase the pressure applied against the pumped fluid and expel it from the first pumping chamber section and decreasing the volume of the second pumping chamber section to decrease the pressure applied against the pumped fluid and draw it into the first pumping chamber section;
a first valve positioned between the input passageway and the passageway network and responsive to the pressure of the pumped fluid in the first pumping chamber section;
a second valve positioned in the passageway network for being responsive to the pressure of the pumped fluid in the first pumping chamber section, the first valve being opened when the second valve closes and the first valve being closed when the second valve opens;
a third valve coupled between the exit passageway and the second valve in the passageway network for preventing pumped fluid flow through the pump member in response to a pressure head at the input or exit ports, the third valve coupled for closing at least one of the first, second, or third valves in response to the head pressure at the input and exit ports;

a second diaphragm bifurcating the priming-damping chamber to define a first priming chamber section for receiving the pumped fluid and a second priming chamber section for receiving the second pumping fluid, the first priming chamber section being interconnected to the passageway network between the second and third valves whereby the pressure of the pumped fluid in the exit passageway is altered in response to deflections of the second diaphragm.

2. The pumping apparatus of claim 1 further comprising:
a pressure transducer coupled to sense variations in the pressure of the second pumping fluid and generating an electronic signal representative of the variations in the pressure of the second pumping fluid;
a pulse generator coupled to receive the electronic signal whereby the pulse generator generates a signal having intermittent electrical pulses having a pulse width, pulse repetition frequency and pulse amplitude, at least one of which is altered in response to the electronic signal;
a heater coupled to intermittently generate heat in response to the intermittent electrical pulses.

3. The pumping apparatus of claim 1 further comprising:
means for maintaining the second pumping fluid at a substantially constant pressure for enabling the second diaphragm to move in response to variations in pressure of the pumped fluid for damping and smoothing the variations in the pressure of the pumped fluid expelled from the exit port.

4. The pumping apparatus of claim 1 wherein each of the first, second and third valves comprises:
a valve chamber defining a valve volume therein;
a valve boss extending into the valve volume having a passageway port in the end thereof; and
a valve diaphragm bifurcating the valve volume for defining a fluid flow section and a fluid pressure section, the valve diaphragm positioned in a normally closed configuration over the passageway port of the valve boss for preventing pumped fluid flow through the passageway port into the fluid flow section.

5. The pumping apparatus of claim 4 wherein the passageway network further comprises:
a first pressure equalizing passageway interconnecting the fluid pressure section and the fluid flow section of the first valve;
a second pressure equalizing passageway interconnecting the fluid pressure section and the fluid flow section of the second valve;
a third pressure equalizing passageway interconnecting the fluid pressure section of the third valve to the input passageway;
a first flow passageway interconnecting the fluid flow section of the first valve and the first pumping chamber section of the pumping chamber;
a second flow passageway interconnecting the passageway port of the second valve and the first pumping chamber section of the pumping chamber; and
a third flow passageway interconnecting the fluid flow sections of the second and third valves and the first priming chamber section, the passageway port of the third valve being a terminus of the exit passageway and the passageway port of the first valve being a terminus of the input passageway.

6. The pumping apparatus of claim 1 or 5 wherein the variable pressure means is responsive to an external source of electrical power, and comprises:
an enclosure interconnected to the second pumping chamber section for containing a quantity of the first pumping fluid;
heater means in the enclosure for being interconnected to the external source of the electrical power, and for intermittently heating the first pumping fluid and increasing the volume of the first pumping fluid to displace the first diaphragm and increase the volume of the second pumping chamber section.

7. A pumping apparatus for moving a pumped fluid from a reservoir to a destination in response to variations of the pressure of either a first pumping fluid or a second pumping fluid comprising:
an input passageway for receiving pumped fluid from the reservoir;
an exit passageway for expelling pumped fluid to the destination;
a pumping means defining a first chamber with a first volume;
a first diaphragm for bifurcating the first chamber into a first section for receiving the pumped fluid through the input passageway and a second section for receiving the first pumping fluid, the first diaphragm being movable in response to variations in the pressure of the first pumping fluid in the second section;
unidirectional flow control means for transferring pumped fluid through the pumping apparatus in only one direction comprising:
a first valve for controlling the flow of pumped fluid into the pumping apparatus in response to movement of the first diaphragm, and
a second valve for controlling the flow of pumped fluid out from the pumping apparatus in response to the movement of the first diaphragm, the first valve opening and the second valve closing in response to first diaphragm movement in one direction and the first valve closing and the second valve opening in response to first diaphragm movement in a second direction;
flow-through prevention means for preventing pumped fluid flow through the pumping apparatus in response to a pressure head in the input passageway or exit passageway comprising:
a third valve interconnected for being closed in response to a pumped fluid head pressure in the input passageway which is larger than the head pressure of the pumped fluid in the exit passageway, the third valve further interconnected for closing one of the first or second valves when the third valve is opened in response to a pumped fluid head pressure in the input passageway which is less than the head pressure of the pumped fluid in the exit passageway; and priming-damping means defining a second chamber with a second volume,
having a second diaphragm for bifurcating the second chamber into a third section for receiving the pumped fluid and a fourth section for receiving the second pumping fluid, the third section being interconnected to the unidirectional flow control means for altering the pressure of the pumped fluid expelled from the exit passageway in response to deflections of the second diaphragm.

8. The pumping apparatus of claim 7 wherein each of the first, second and third valves comprises:
   a valve chamber defining a valve volume therein;
   a valve boss extending into the valve volume having a passageway port in the end thereof; and
   a valve diaphragm bifurcating the valve volume for defining a fluid flow section and a fluid pressure section, the valve diaphragm positioned in a normally closed configuration over the passageway port of the valve boss for preventing pumped fluid flow through the passageway port into the fluid flow section.

9. The pumping apparatus of claim 8 further comprising:
   a first pressure equalizing passageway interconnecting the fluid pressure section and the fluid flow section of the first valve means;
   a second pressure equalizing passageway interconnecting the fluid pressure section and the fluid flow section of the second valve means;
   a third pressure passageway interconnecting the fluid pressure section of the third valve to the input passageway;
   a first flow passageway interconnecting the fluid flow section of the first valve and the first section of the pumping means;
   a second flow passageway interconnecting the passageway port of the second valve and the first section of the pumping means; and
   a third flow passageway interconnecting the fluid flow section of the second and third valves and the third section of the priming-damping means, the passageway port of the third valve being a terminus of the exit passageway and the passageway port of the first valve being a terminus of the input passageway.

10. The pumping apparatus of claims 7 or 9 wherein the apparatus is operable in response to an external electrical power source, further comprising:
   variable pressure means responsive to the external electrical power source for causing intermittent pressure variations in the second pumping fluid, the variable pressure means comprising:
   an enclosure means interconnected to the fourth section for confining the second pumping fluid,
   an electrical heater means in the enclosure for being interconnected to the external electrical power source and intermittently heated to thereby heat the second pumping fluid and increasing the volume of the second pumping fluid to displace the second diaphragm to increase the volume of the fourth section.

* * * * *